United States Patent [19]
Matsushita

[11] Patent Number: 5,340,424
[45] Date of Patent: Aug. 23, 1994

[54] METHOD FOR MAKING DISPOSABLE PANTS

[75] Inventor: Michiko Matsushita, Iyomishima, Japan

[73] Assignee: Uni-Charm Corporation, Ehime, Japan

[21] Appl. No.: 989,386

[22] Filed: Dec. 11, 1992

Related U.S. Application Data

[62] Division of Ser. No. 903,163, Jun. 24, 1992.

[30] Foreign Application Priority Data

Jul. 10, 1991 [JP] Japan .................. 3-195702

[51] Int. Cl.$^5$ .................. A61F 13/15; B32B 31/08
[52] U.S. Cl. .................. 156/164; 156/163; 156/204; 156/227; 156/229; 156/256; 156/267; 2/400; 604/385.2
[58] Field of Search .................. 156/164, 160, 163, 229, 156/204, 227, 256, 267; 604/385.2; 2/400, 406

[56] References Cited

U.S. PATENT DOCUMENTS

| | | | |
|---|---|---|---|
| 2,905,947 | 9/1959 | Rosenberg | 2/406 |
| 2,997,044 | 8/1961 | Simons | 2/406 X |
| 3,142,301 | 7/1964 | Erteszek | 2/406 X |
| 3,332,423 | 7/1967 | Whalen | 2/406 X |
| 3,828,367 | 8/1974 | Bourgeois | 156/164 X |
| 4,606,964 | 8/1986 | Wideman | 156/164 X |
| 4,646,362 | 3/1987 | Heran et al. | 2/400 |
| 4,701,171 | 10/1987 | Boland . | |
| 4,847,134 | 7/1989 | Fahrenkrug et al. | 156/164 X |
| 4,938,753 | 7/1990 | Gompel . | |
| 5,147,487 | 9/1992 | Nomura et al. | 156/229 X |

FOREIGN PATENT DOCUMENTS

| | | |
|---|---|---|
| A-0048011 | 3/1982 | European Pat. Off. . |
| A-0405575 | 1/1991 | European Pat. Off. . |
| A-0417766 | 3/1991 | European Pat. Off. . |
| A-2354064 | 1/1978 | France . |
| 960367 | 6/1964 | United Kingdom . |
| 2195230 | 4/1988 | United Kingdom . |

*Primary Examiner*—Jeff H. Aftergut
*Attorney, Agent, or Firm*—Fred Philpitt

[57] ABSTRACT

This invention effectively avoids the inconvenience conventially occuring such that, with the pants of prior art being put on the user, the front body is displaced downward under a force exerted thereon as the user's legs move or under a weight of excretions accumulated in the crotch area of the pants, resulting in loosened leg-openings through which leak of excretion may occur.

A front body comprising a sheet having elastic stretchability in the transverse direction and a rear body comprising a sheet having no elastic stretchability are bonded to each other with a transverse dimension of the front body in its transversely contracted state being smaller than a transverse dimension of the rear body so that laterally opposite waist sides of the user's body wearing the pants may be covered by a part of the rear body.

3 Claims, 4 Drawing Sheets

METHOD FOR MAKING DISPOSABLE PANTS

CROSS REFERENCE TO RELATED APPLICATIONS

This application is a division of U.S. Ser. No. 07/903,163 filed Jun. 24, 1992, pending.

BACKGROUND OF THE INVENTION

The present invention relates to disposable pants, for example, in the form of training pants for babies, pants type diaper or sanitary pants, and method for making them.

For the conventional disposable pants, for example, disposable training pants, it is well known to form the entire front and rear bodies from elastically stretchable sheet material such as nonwoven fabric or to form only opposite side portions of the front and rear bodies from such sheet material.

However, all of such well known pants are elastically stretchable at least along laterally opposite sides and, in consequence, the front body is apt to be displaced downward under a force exerted thereon as the user's legs move or under weight of excretions accumulated in a crotch area of the pants. Such downward displacement of the front body results in not only unsighted appearance of wearing but also loosened leg-openings through which leak of excretions may occur.

SUMMARY OF THE INVENTION

It is a principal object of the invention to configure pants using an elastically stretchable sheet so as to minimize said downward displacement of the front body.

The object set forth above is achieved, in accordance with the present invention, by disposable pants comprising a front body made of a sheet having elastic stretchability at least in the transverse direction and a rear body made of a sheet having substantially no elastic stretchability, which are bonded to each other with a transverse dimension of said front body being smaller than a transverse dimension of said rear body so that laterally opposite waist sides of the user wearing the pants may be covered by a part of the rear body. If it is required for the pants, e.g., training pants or diaper of pants-type, to absorb and hold excretions, for example, urine, liquid-impermeable sheets may be used as outer sheets of the front and rear bodies, respectively, while a single non-bonded continuous liquid-permeable sheet having substantially no elastic stretchability may be used as an inner sheet common to the front and rear bodies, and a liquid absorbent core may be sandwiched between these inner and outer sheets, if desired.

While, according to the present invention, elastically stretchable members may be provided, if desired, around the waist-opening and the leg-openings of the pants in order to tighten these areas, use of such elastically stretchable members is not essential to the invention.

With the pants of the invention being put on the user, the laterally opposite sides of the user's waist are covered by a part of the rear body having substantially no elastic stretchability and a transverse contractile force of the front body extending between said laterally opposite sides of the user's waist and having elastic stretchability at least in the transverse direction causes the entire pants to fit around the user's body. Said laterally opposite sides function as means to hold the pants on the user's body. The front body located on the user's belly side freely contracts as the user breathes out.

BRIEF DESCRIPTION OF THE DRAWINGS

The pants constructed in accordance with the present invention and the method for making them will be described by way of example in reference with the attached drawings, in which.

PREFERRED EMBODIMENTS OF THE INVENTION

Embodiment of the Pants

Figure 1:
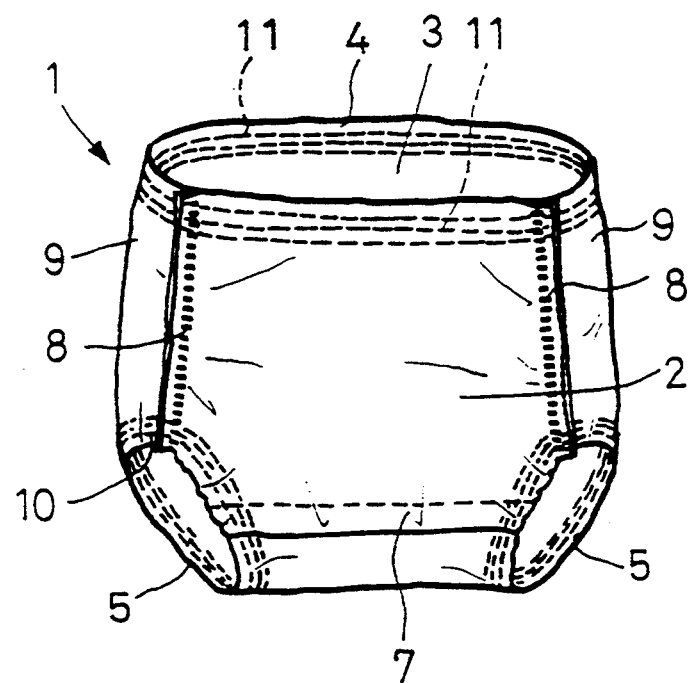
FIG. 1 is a perspective view showing pants constructed according to a first embodiment of the method of the present invention.

Referring to FIG. 1, the most basic pants 1 constructed according to the method of the invention is illustrated.

The pants 1 comprise a front body sheet 2 which is elastically stretchable at least in the transverse direction (or both in breadth and length) and a rear body sheet 3 which is not substantially elastically stretchable. The pants have a waist-opening 4 and a pair of leg-openings 5. In FIG. 1, the front body sheet 2 is shown to be contracted in the transverse direction and, at such state, has a transverse dimension smaller than that of the rear body sheet 3. The front body sheet 2 is smaller than the rear body sheet 3 also in a longitudinal dimension. Longitudinal ends of the front and rear body sheets 2, 3 are overlapped on and bonded to each other by a continuous seal line 7 extending along such overlapped area.

Respective transversely opposite sides of the front and rear body sheets 2, 3 have their inner surfaces overlapped on and bonded to each other by respective intermittent seal lines 8 extending along these overlapped areas.

With the front body sheet 2 being contracted in the transverse direction as in FIG. 1, laterally opposite sides 9 of the pants 1 are defined by a part of the rear body sheet 3 and the bonded areas (seal lines 8) of said laterally opposite sides 9 lie on the belly side. Obviously, the front body sheet 2 is laterally stretched and then contracted again as the pants 1 are put on the user. Transverse dimensional ratio of the front body sheet 2 and the rear body sheet 3 as well as transverse elongation rate of the front body sheet 2 are selected so that said bonded areas 8 as well as said laterally opposite sides 9 may be positioned as mentioned just above once the pants have been put on the user.

Elastically stretchable members 10, 11 each comprising a plurality of thread-like elastic elements are attached in their longitudinally stretched states around the leg-openings 5 and the waist-opening 4, respectively.

Though not shown, a single continuous inner sheet which is common to the front and rear bodies and has substantially no elastic stretchability may be dot-bonded at desired intervals to the inner side of said front and rear body sheets 2, 3, if desired, so as not to interfere with the elastic stretchability of said front body sheet 2. In this case, a liquid-impermeable sheet is used as said outer sheet while a liquid-permeable sheet is used as said inner sheet and laterally opposite sides of said inner sheet are bonded to said laterally opposite ends of the front and rear body sheets 2, 3 in the manner as has previously mentioned. Also in this case, a liquid absorbent core may be sandwiched between the inner and outer sheets, if desired.

Embodiment 1 of the Method for Making the Pants

Figure 2:
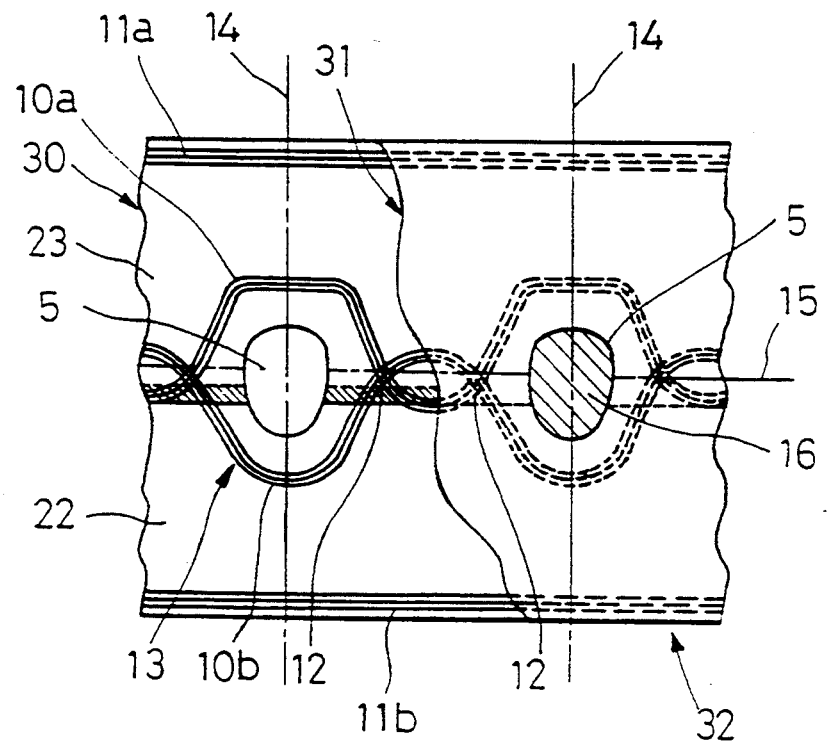
FIG. 2 is a partial plan view illustrating some steps followed by said first embodiment, i.e., bonding a front body web and a rear body web together to form a web for an outer sheet of the pants, providing this web for the outer sheet with elastically stretchable members around a waist and legs, respectively, laying a web for an inner sheet of the pants on said web for the outer sheet, and forming leg-openings.
Figure 3:
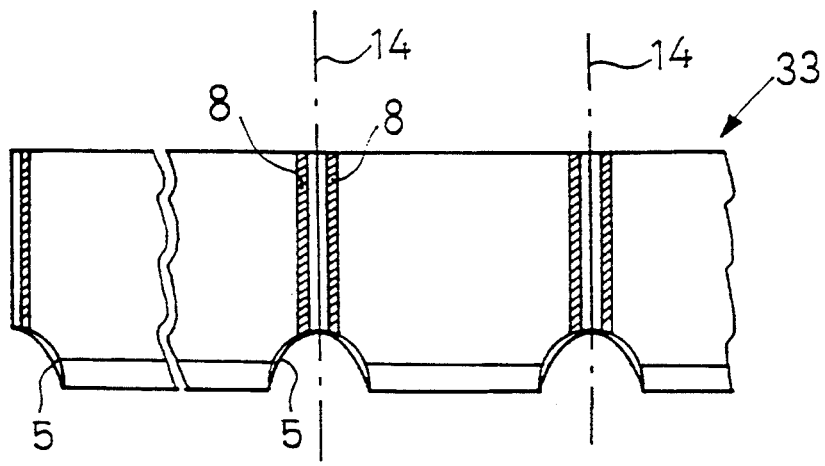
FIG. 3 is a partial plan view of the web assembly shown in FIG. 2 as having been folded along a longitudinal center line and provided at desired locations with seals for opposite sides of the individual pants.
Figure 4:
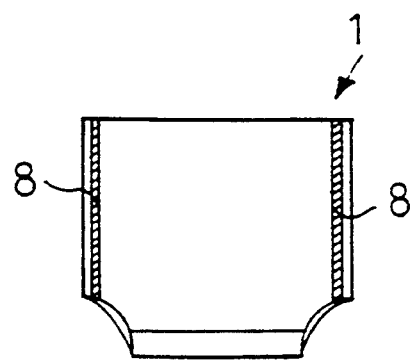
FIG. 4 is a plan view of the individual pants obtained by cutting the web of FIG. 3.

Referring to FIGS. 2 through 4, respective steps in the method of the present invention are illustrated. A front body web 22 having elastic stretchability at least in the transverse direction is transferred to an assembly station (not shown) as said web 22 is longitudinally stretched by a desired elongation rate, for example 1.05 to 1.5 times, while a rear body web 23 having a width appropriately larger than said web 22 and having substantially no elastic stretchability is transferred to said assembly station so that one longitudinal side edge of said web 23 may be overlapped on one longitudinal side edge of said web 22 which is being stretched and this overlapped area may be bonded together by the continuous seal line 7 so as to provide web 30 defining the outer sheet. Such bonding may be achieved by using hot melt adhesive, or thermal or supersonic welding technique.

Stretching of said web 22 may be achieved, for example, as conventionally employed in stretching of the elastically stretchable members to be attached around the respective leg-openings of disposable diaper or the like, by increasing the circumferential velocity of one pair of nip-rolls located upstream with respect to the direction in which said web 22 is transferred to nip said web therebetween and thereby to transfer it, relative to the circumferential velocity of the other pair of similar nip-rolls located downstream.

Two continuous elastically stretchable members 10a, 10b each comprising a plurality of thread-like elastic elements are placed on and attached to the web 30 traveling toward said assembly station along the central while said members 10a, 10b are longitudinally stretched by a desired elongation rate, for example 1 to 3 times so that the respective members 10a, 10b describe sine curves partially crossing each other. Simultaneously, another pair of continuous elastically stretchable members 11a, 11b each comprising a plurality of thread-like elastic elements are placed on and attached to said web 30 along the areas adjacent longitudinally opposite side edges.

Placement of the elastically stretchable members 10a, 10b, 11a, 11b in the configuration as mentioned above may be achieved, as disclosed by the applicant of this application in European Patent Application No. 0405575 A1, by utilizing a pair of traverse means. Attaching of these elastically stretchable members to the web 30 may be achieved by previously applying hot melt adhesive on the web 30 along loci to be described by the respective elastically stretchable members or by applying such adhesive directly on these elastically stretchable members. The portions of the respective elastically stretchable members 10a, 10b defined between a pair of adjacent crossings thereof may be free from adhesive so that these portions are not attached to the web 30 and, in addition, each of said portions may be cut at one location so that these portions may be snapped back.

An inner sheet web 31 having a substantially same width as the web 30 traveling toward said assembly station and having substantially no elastic stretchability is put on and bonded to said web 30 to form a web 32. Such bonding may be also achieved by use of hot melt adhesive, or thermal or supersonic welding technique.

From each annular zone 13 defined by the elastically stretchable members 10a, 10b, a portion 16 having a desired size and a shape being symmetric with respect to an imaginary center line 14 extending across the web 32 transversely of the traveling direction of said web 32 is cut out to form each of the leg-opening 5.

The web 32 thus formed with the leg-openings 5 is folded in two along a longitudinal imaginary center line 15 with the web 31 facing inward and provided with intermittent seal lines 8 extending adjacent each of said imaginary center lines 14 and thereby the web 31 and the web 32 are bonded to each other so as to form a web 33.

The web 33 being moved toward said assembly station is successively cut together with the elastically stretchable members 10a, 10b, 11a, 11b along respective said imaginary center lines 14 each extending in parallel and between each pair of adjacent seal lines 8 and thereby the individual pants are obtained.

Each of the leg-openings 5 may be formed, instead of forming them immediately after formation of the web 32, immediately after formation of the web 33 or during operation of cutting the web 33 into the individual pants.

The outer sheet web 30 may be made of liquid-impermeable material such as plastic film and particularly the web 23 making a part of the web 30 may be made of moisture-permeable and air-permeable material. The inner sheet web 31 may be made of fibrous nonwoven fabric. It should be understood that, as has been described in reference with FIG. 1, the most basic configuration of the pants does not use the inner sheet web 31, i.e., only the web 30 is used as the material for the component sheets of the pants and, in such cases, the webs 22, 23 forming together the web 30 may be preferably of nonwoven fabric. While the elastically stretchable members 10, 11 may comprise natural or synthetic rubber or the like, these elastically stretchable members are sometimes eliminated in the most basic pants 1.

Embodiment 2 of the Method for Making the Pants

Figure 5:
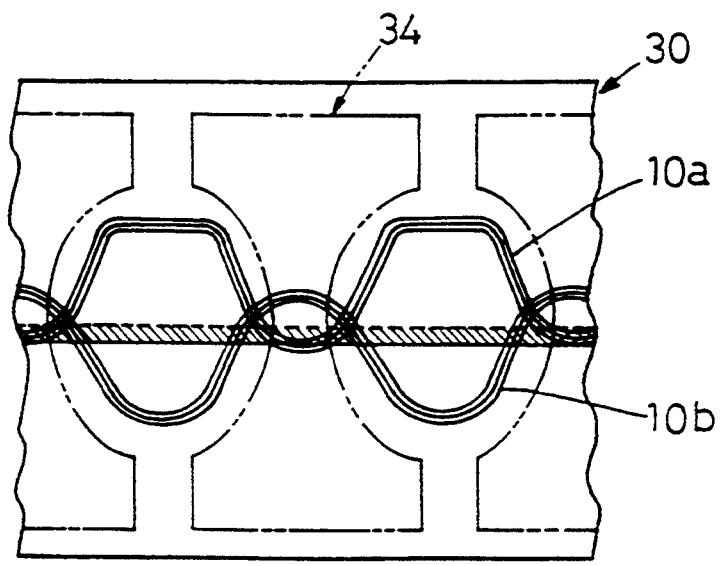
FIG. 5 is a partial plan view illustrating some steps followed by a second embodiment of the method of the present invention, i.e., bonding the front body web and the rear body web together to form the web for the outer sheet of the pants, providing this web for the outer sheet with elastically stretchable members around legs, and further providing said web for the outer sheet with an absorbent core.
Figure 6:
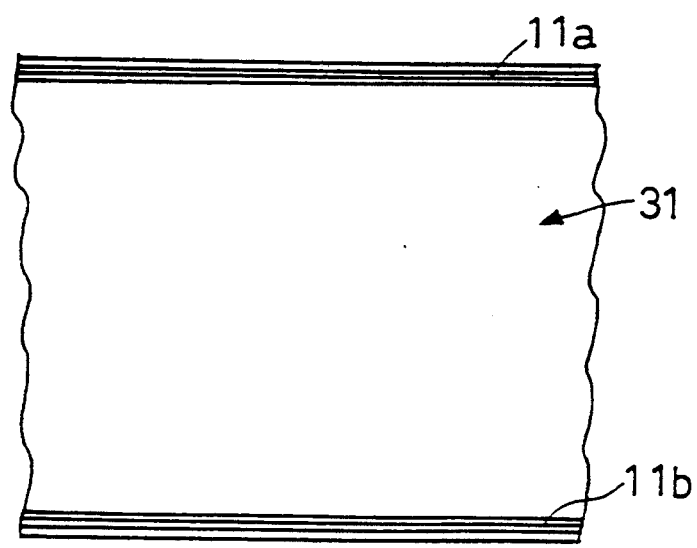
FIG. 6 is a partial plan view illustrating one step followed by said second embodiment, i.e., providing said web for the inner sheet of the pants with an elastically stretchable member around the waist.
Figure 7:
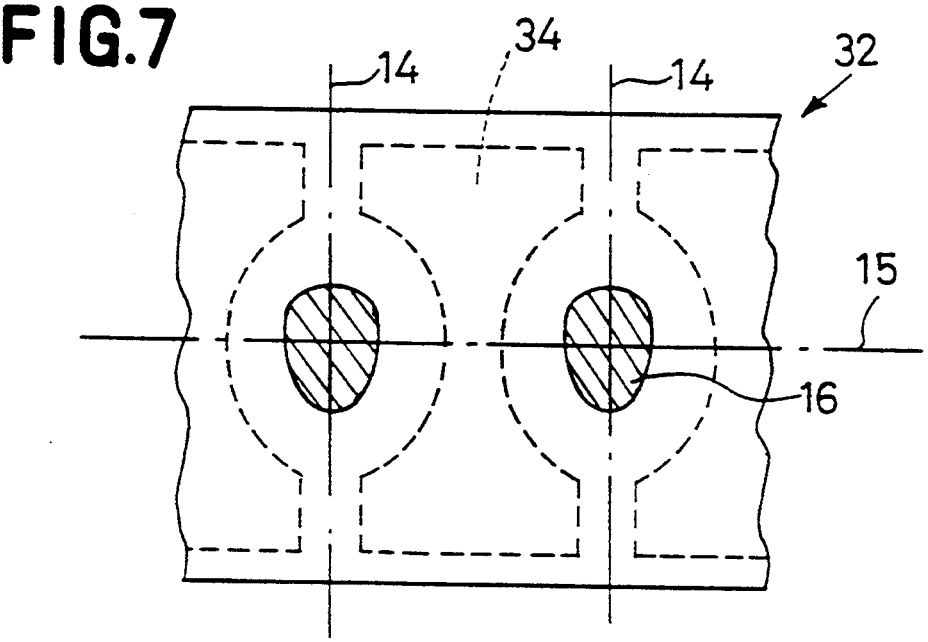
FIG. 7 is a partial plan view showing the web of FIG. 6 laid on the web of FIG. 5.
Figure 8:
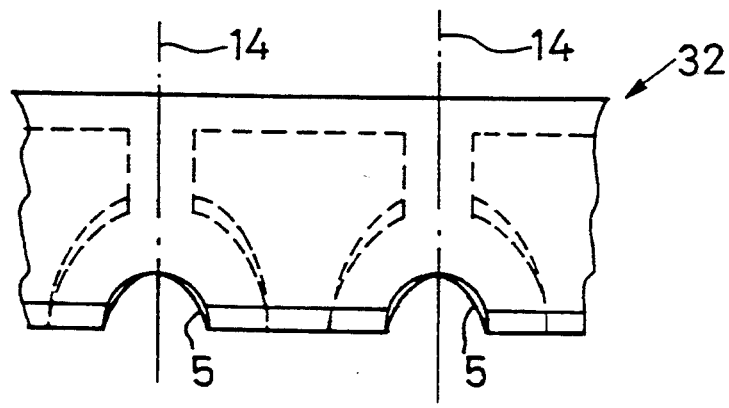
FIG. 8 is a partial plan view of the web shown in FIG. 7 as having been folded in two along a longitudinal center line and formed with leg-openings.
Figure 9:
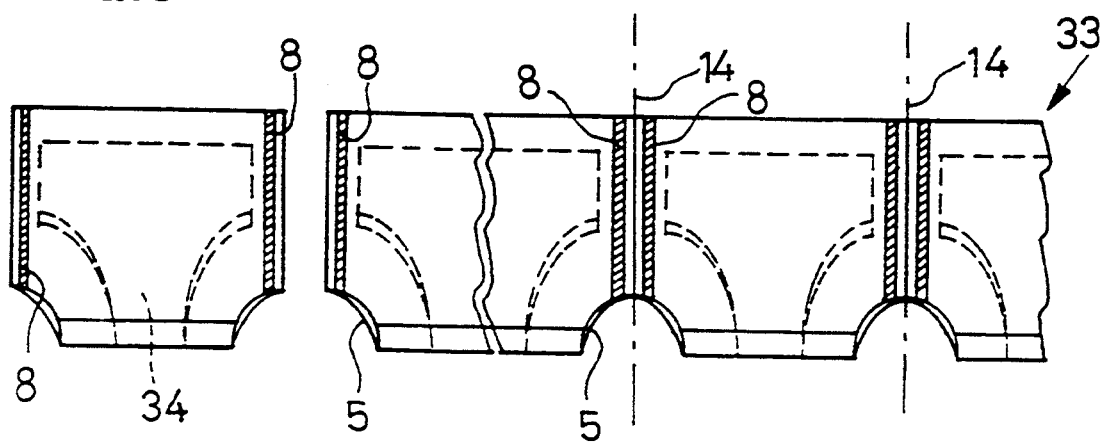
FIG. 9 is a combination of a partial plan view of the web shown in FIG. 8 as having been provided at desired locations with seals for laterally opposite sides of the pants and a plan view of said web as having been cut to obtain individual pants.

This embodiment 2 is similar to said Embodiment 1 except that a liquid absorbent core 34 performed in an hourglass-shape is placed between each pair of adjacent annular zones 13 defined by the elastically stretchable members 10a, 10b, as indicated by a chain line in FIG. 5, before the web 31 is put on the web 30; the elastically stretchable members 11a, 11b are placed on and bonded to the inner surface of the web 31, as shown in FIG. 6; and each leg-opening 5 is formed, as apparent from FIGS. 7 through 9, by partially cutting off the web 32 after it is folded in two along the longitudinal imaginary center line 15. Therefore, the parts corresponding to those said in Embodiment 1 are designated by the same reference numerals as those designating the corresponding parts in Embodiment 1 and this Embodiment 2 will not be further described in details. The core 34 preferably comprises crushed pulp mixed with thermoplastic fibre and super absorption polymer powder and molded into a desired shape.

With the pants of the invention put on the user, opposite waist sides of the user's body are covered by a part of the rear body having substantially no elastic stretchability and a transverse contractile force of the front body defined between said opposite waist sides and having elastic stretchability at least in the transverse direction causes the entire pants to fit around the user's body. Thus, these opposite waist sides function as means to hold the pants on the user's body and thereby to avoid the inconvenience conventionally occurring due to unstable stretchability of said opposite waist sides such that the front body is displaced downward under a force exerted thereon as the user's legs move or under weight of excretions accumulated in the crotch area of the pants, resulting not only in unsightly appearance of wearing but also in loosened leg-openings through which leak of excretions may occur.

The pants having such advantages can be easily made by the method according to the invention by overlapping one longitudinal side edge of the second web for the rear body having substantially no elastic stretchability on one longitudinal side edge of the first web for the front body having the elastic stretchability at least in the transverse direction while said first web is longitudinally elongated, and then providing this overlapped area with the seal to bond these webs to each other.

What is claimed is:

1. A method for forming disposable pants, said method comprising the steps of:
   (a) moving an elongated first web (22) along a first path, said first web (22) having spaced apart longitudinal side edges,
   (b) moving an elongated second web (23) along a parallel second path, said second web (23) also having spaced apart longitudinal side edges,
   (c) said first web (22) having elastic stretchability and being maintained in a stretched condition while moving along said first path,
   (d) said second web (23) having substantially no elastic stretchability,
   (e) overlapping one longitudinal side edge of said first web (22) with one longitudinal edge of said second web and bonding said overlapping longitudinal side edges together along a first seal line (7) while maintaining said first web (22) in a stretched condition to thereby form an enlarged third web (30) that is larger than either said first web (22) or said second web (23),
   (f) folding said enlarged third web (30) in two along a longitudinal imaginary center line (15) and then sealing this folded web (33) transversely thereof at regular intervals to form a folded web (33) with a plurality of spaced apart second seals (8),
   (g) cutting said folded web (33) along a plurality of cut lines (14) that are parallel to each of said second seals (8) to thereby obtain individual pants with portions of said second seals (8) remaining along the laterally opposite sides thereof; and
   (h) partially cutting off folded web (33) along spaced apart portions of said longitudinal imaginary center line (15) to thereby form leg-openings (5) immediately after the formation of said folded web (33) or during the step of cutting said folded web (33) into individual pants, the individual pants resulting from the method having a front body (2) formed from said first web (22) and a rear body (3) formed from said second web (23), said front body being smaller in area than said rear body (3) because said first web (22) has resumed an unstretched state.

2. A method for forming disposable pants, said method comprising the steps of:
   (a) moving an elongated first web (22) along a first path, said first web (22) having spaced apart longitudinal side edges,
   (b) moving an elongated second web (23) along a parallel second path, said second web (23) also having spaced apart longitudinal side edges,
   (c) said first web (22) having elastic stretchability and being maintained in a stretched condition while moving along said first path,
   (d) said second web (23) having substantially no elastic stretchability,
   (e) overlapping one longitudinal side edge of said first web (22) with one longitudinal edge of said second web and bonding said overlapping longitudinal side edges together along a first seal line (7) while maintaining said first web (22) in a stretched condition to thereby form an enlarged third web (30) that is larger than either said first web (22) or said second web (23),
   (f) laying a fourth web (31) having substantially no elastic stretchability on said enlarged third web (30) to form a composite web (32),
   (g) folding said composite web (32) in two along a longitudinal imaginary center line (15) and then sealing the resulting folded web (33) transversely thereof at regular intervals to form a folded web (33) with a plurality of spaced apart second seals (8),
   (h) cutting said folded web (33) along a plurality of cut lines (14) parallel to each of said second seals (8) to obtain individual pants with portions of said second seals (8) remaining along the laterally opposite sides thereof; and
   (i) partially cutting off said composite web (32) or folded web (33) along spaced apart portions of said longitudinal imaginary center line (15) to thereby form leg-openings (5) immediately after the formation of said composite web (32) or said folded web (33) or during the step of cutting said folded web

(33) into individual pants the individual pants resulting from the method having a front body (2) formed from said first web (22) and a rear body (3) formed from said second web (23), said front body being smaller in area than said rear body (3) because said first web (22) has resumed an unstretched state.

3. A method as recited in claim 2 which further includes the step of sandwiching liquid absorbent cores between said third (30) and fourth webs (31) in areas corresponding to the individual pants before folding said composite web (32) in two as set forth in step (g).

* * * * *